(12) United States Patent
Prue et al.

(10) Patent No.: US 12,042,612 B2
(45) Date of Patent: Jul. 23, 2024

(54) SPLIT SHEATH INTRODUCER AND METHOD OF MANUFACTURING A SPLIT SHEATH INTRODUCER

(71) Applicant: Argos Corporation, Taunton, MA (US)

(72) Inventors: Jim Prue, Griswold, CT (US); Perry Cicalis, Bridgewater, MA (US)

(73) Assignee: ARGOS CORPORATION, Taunton, MA (US)

( * ) Notice: Subject to any disclaimer, the term of this patent is extended or adjusted under 35 U.S.C. 154(b) by 0 days.

(21) Appl. No.: 17/723,585

(22) Filed: Apr. 19, 2022

(65) Prior Publication Data

US 2022/0233826 A1     Jul. 28, 2022

Related U.S. Application Data

(63) Continuation of application No. 16/233,601, filed on Dec. 27, 2018, now Pat. No. 11,344,705.

(60) Provisional application No. 62/610,616, filed on Dec. 27, 2017.

(51) Int. Cl.
| | |
|---|---|
| *A61M 25/06* | (2006.01) |
| *A61M 25/00* | (2006.01) |
| *B29C 48/00* | (2019.01) |
| *B29C 48/20* | (2019.01) |
| *C08K 5/54* | (2006.01) |
| *C08L 23/06* | (2006.01) |

(52) U.S. Cl.
CPC .... *A61M 25/0668* (2013.01); *A61M 25/0009* (2013.01); *B29C 48/00* (2019.02); *B29C 48/20* (2019.02); *C08K 5/54* (2013.01); *C08L 23/06* (2013.01); *C08L 2207/04* (2013.01)

(58) Field of Classification Search
CPC ...... A61M 25/0668; A61M 2025/0675; A61M 25/01; A61M 25/0009; A61F 2/97; B29C 48/00; B29C 48/20; B29C 48/09; B29C 48/19; B29C 48/32; B29C 48/49; B29C 48/916; C08K 5/54; C08L 23/06; C08L 2207/04
USPC ...................................... 604/164.05
See application file for complete search history.

(56) References Cited

U.S. PATENT DOCUMENTS

| | | | | |
|---|---|---|---|---|
| 4,402,685 A | * | 9/1983 | Buhler | A61M 25/0009 525/931 |
| 4,421,867 A | * | 12/1983 | Nojiri | C08J 9/0014 521/88 |
| 4,781,690 A | * | 11/1988 | Ishida | A61L 31/06 604/528 |

(Continued)

FOREIGN PATENT DOCUMENTS

| WO | WO0015289 | * | 3/2000 |
| WO | WO2016196511 | * | 12/2016 |

*Primary Examiner* — Jeffrey M Wollschlager
(74) *Attorney, Agent, or Firm* — Grogan, Tuccillo & Vanderleeden LLP

(57) ABSTRACT

A splittable introducer sheath includes a tubular body portion formed from a first material and at least one stripe extending an entire length of the main body portion, the at least one stripe being formed form a second material. The first material is one of a medium-density polyethylene modified with a friction-reducing additive or high-density polyethylene (HDPE) modified with a friction-reducing additive. The second material is a thermoplastic elastomer modified with a siloxane additive. The sheath is dividable longitudinally along the at least one stripe.

11 Claims, 7 Drawing Sheets

(56) References Cited

U.S. PATENT DOCUMENTS

| | | | | |
|---|---|---|---|---|
| 4,874,374 | A * | 10/1989 | Kousai | B29C 48/335 |
| | | | | 604/528 |
| 5,104,388 | A * | 4/1992 | Quackenbush | A61M 25/0668 |
| | | | | 604/164.05 |
| 9,126,019 | B2 * | 9/2015 | Guo | A61M 25/005 |
| 2006/0041230 | A1 * | 2/2006 | Davis | A61M 25/0009 |
| | | | | 604/160 |
| 2008/0208128 | A1 * | 8/2008 | Guo | A61M 25/001 |
| | | | | 604/164.05 |
| 2010/0092793 | A1 * | 4/2010 | Aithani | B32B 27/00 |
| | | | | 428/483 |
| 2010/0310892 | A1 * | 12/2010 | German | C08L 23/08 |
| | | | | 525/240 |
| 2013/0184659 | A1 * | 7/2013 | Byrnes | A61M 25/0045 |
| | | | | 264/211.12 |
| 2015/0133953 | A1 * | 5/2015 | Seifert | A61B 17/3468 |
| | | | | 606/129 |
| 2016/0374743 | A1 * | 12/2016 | Beasley | A61B 18/1492 |
| | | | | 606/27 |
| 2018/0371250 | A1 * | 12/2018 | Karube | C08L 91/00 |
| 2019/0208861 | A1 * | 7/2019 | Shimizu | A43B 13/04 |
| 2023/0043006 | A1 * | 2/2023 | Sawano | B32B 15/20 |
| 2023/0051902 | A1 * | 2/2023 | Lee | H01M 4/366 |

* cited by examiner

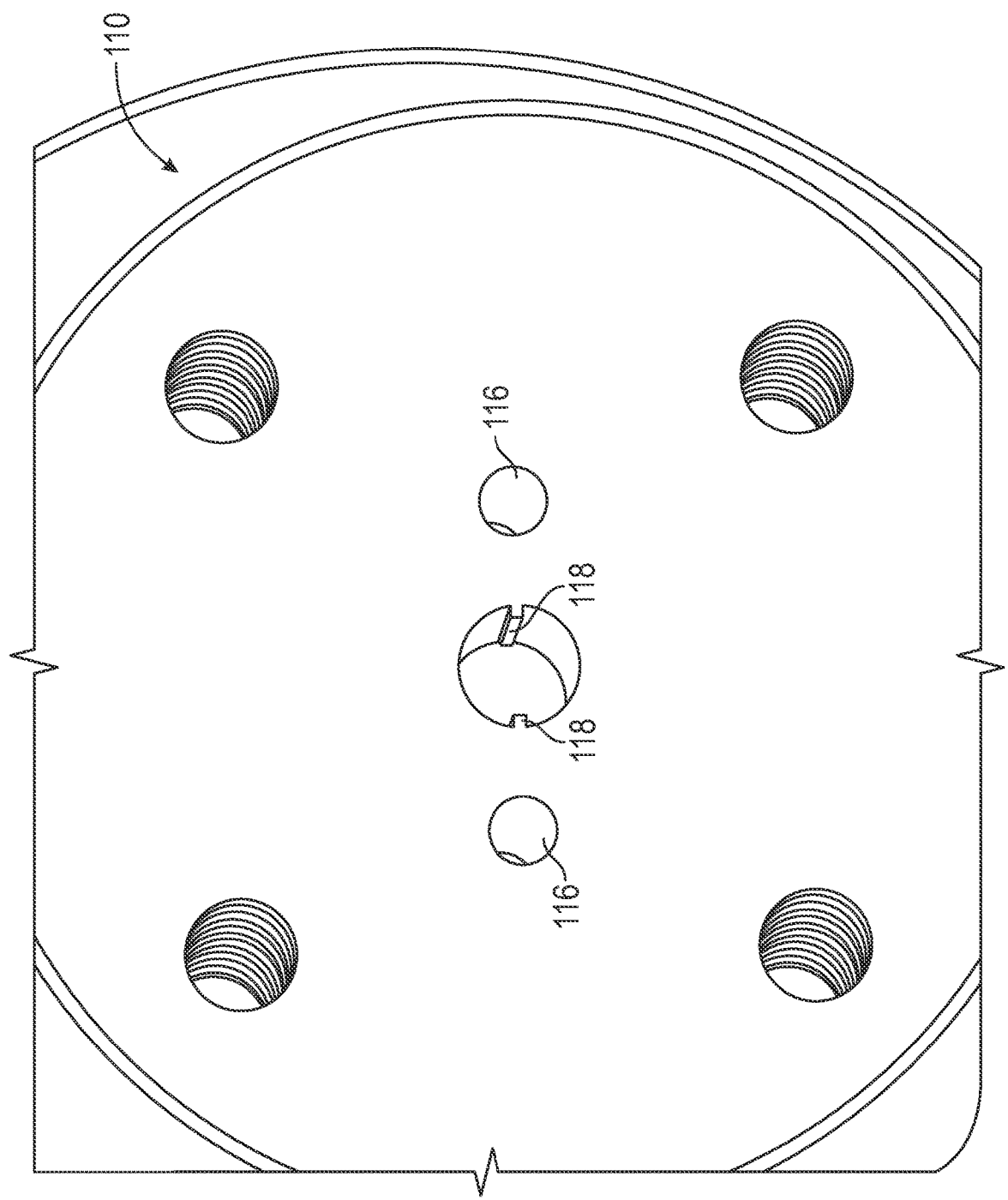

SPLIT SHEATH INTRODUCER AND METHOD OF MANUFACTURING A SPLIT SHEATH INTRODUCER

CROSS-REFERENCE TO RELATED APPLICATIONS

This application is a continuation application of U.S. patent application Ser. No. 16/233,601, filed on Dec. 27, 2018, which claims the benefit of U.S. Provisional Application Ser. No. 62/610,616, filed on Dec. 27, 2017, both of which are hereby incorporated by reference herein in their entireties.

FIELD OF THE INVENTION

The present invention relates generally to medical devices and, more particularly, to a splittable or peelable sheath used for the introduction of catheters and other medical devices into a patient, and a method of manufacturing such a sheath.

BACKGROUND OF THE INVENTION

A variety of medical procedures involve or require the introduction of devices through the skin and underlying tissue layers into blood vessels or other locations inside the body of a patient. These purposes include, for example, the introduction of catheters, pacemaker leads and other such devices into a patient's body. These devices are transcutaneous devices which pass through the skin and into the blood vessel during use.

A number of systems and device have been developed to aid in the placement of such devices into the body of a patient. Once such device, known as an introducer set, includes a peel away introducer sheath and a dilator. The peel away introducer sheath is a thin-walled, usually cylindrical, device that is placed in position so that it provides a communicating passageway through the tissue. This is accomplished by fitting the introducer sheath tightly over the dilator and advancing both devices through the tissue together as a unit. The long, tapered tip of the dilator acts to stretch the opening in the skin and blood vessel to allow for the insertion of the larger sheath. The dilator is then removed, leaving the introducer sheath alone in the desired position, acting to hold the penetrated site open. At that point, the catheter tube or other invasive device is advanced through the introducer sheath into the desired position. The peel away introducer sheath is then removed from the tissue and pulled apart lengthwise into two pieces, separating it from the inserted device.

Existing peelable introducer sheaths are typically formed from polypropylene or polyethylene tubing and have a score line imparted along the length of the sheath. After application/insertion, the sheath can be pulled apart along the score line so that the sheath can be removed. With such polypropylene or polyethylene tubing, however, tearing or peeling of the sheath along the score line can be difficult or cumbersome to initiate, and often produces a jagged tear along the score line, which is undesirable. Other known sheaths are manufactured from Teflon, which has a propensity to tear linearly on its own (i.e., without the need for a score line). Teflon, however, is an expensive material that inhibits its widespread use in such devices.

Other efforts to produce peelable or splittable introducer sheaths have involved using co-extrusion and/or injection molding processes to form a tubular sheath with longitudinal stripes of a different material than the main body of the sheath, which are intended to allow for easy peeling along the length of the sheath at the stripe/main body interface. Existing manufacturing processes, tooling and materials utilized in the manufacture of such sheaths have not, however, succeeded in producing a reliable product. In particular, despite such introducer sheaths (with opposing stripes along which the sheath is intended to be peeled) having been invented almost 30 years ago, such sheaths are not in use today due to a number of problems and unique constraints that have heretofore not been overcome or met.

For example, the sheath of an introducer must be internally lubricous to allow for dilators, catheters and other devices to easily slide therethrough and into the body of a patient. In addition, the stripes must be weaker than the material of the main body, and must be able to peel easily while at the same time form a reliable attachment to the main body prior peeling to prevent inadvertent detachment during insertion of the sheath and dilator. To date, stripe materials that are able to provide this functionality have been inherently tacky, which can create a problem with ovality (i.e., the sheath not being round) in the tube while processing.

In view of the above, there is a long-felt need in the art for an effective means of manufacturing a peelable or splittable sheath that has a lubricous interior, is able to be easily split when desired, but which resists inadvertent splitting during insertion, is substantially round, has minimal tackiness, and has peel stripes of minimal width. Despite the desire of others to provide a splittable sheath with the characteristics indicated above for quite some time, to date, efforts directed to this end have failed to produce a saleable and useable product.

SUMMARY OF THE INVENTION

It is an object of the present invention to provide a splittable or peelable introducer sheath.

It is an object of the present invention to provide a splittable or peelable introducer sheath that has a lubricous interior.

It is an object of the present invention to provide a splittable or peelable introducer sheath that is able to be easily split when desired, but which resists inadvertent splitting during insertion.

It is an object of the present invention to provide a splittable or peelable introducer sheath that is substantially round.

It is an object of the present invention to provide a splittable or peelable introducer sheath that has a peel stripe of minimal width.

It is another object of the invention to provide a method of manufacturing a splittable or peelable sheath having the specific combination of characteristics described above.

These and other objects are achieved by the present invention.

In an embodiment, a splittable introducer sheath includes a tubular body portion formed from a first material and at least one stripe extending an entire length of the main body portion, the at least one stripe being formed form a second material. The first material is one of a medium-density polyethylene modified with a friction-reducing additive or high-density polyethylene (HDPE) modified with a friction-reducing additive. The second material is a thermoplastic elastomer modified with a siloxane additive. The sheath is dividable longitudinally along the at least one stripe.

BRIEF DESCRIPTION OF THE DRAWINGS

The present invention will be better understood from reading the following description of non-limiting embodiments, with reference to the attached drawings, wherein below:

FIG. 5 is an enlarged, front perspective view of the die of FIG. 4.

DETAILED DESCRIPTION OF THE PREFERRED EMBODIMENT

Figure 1:
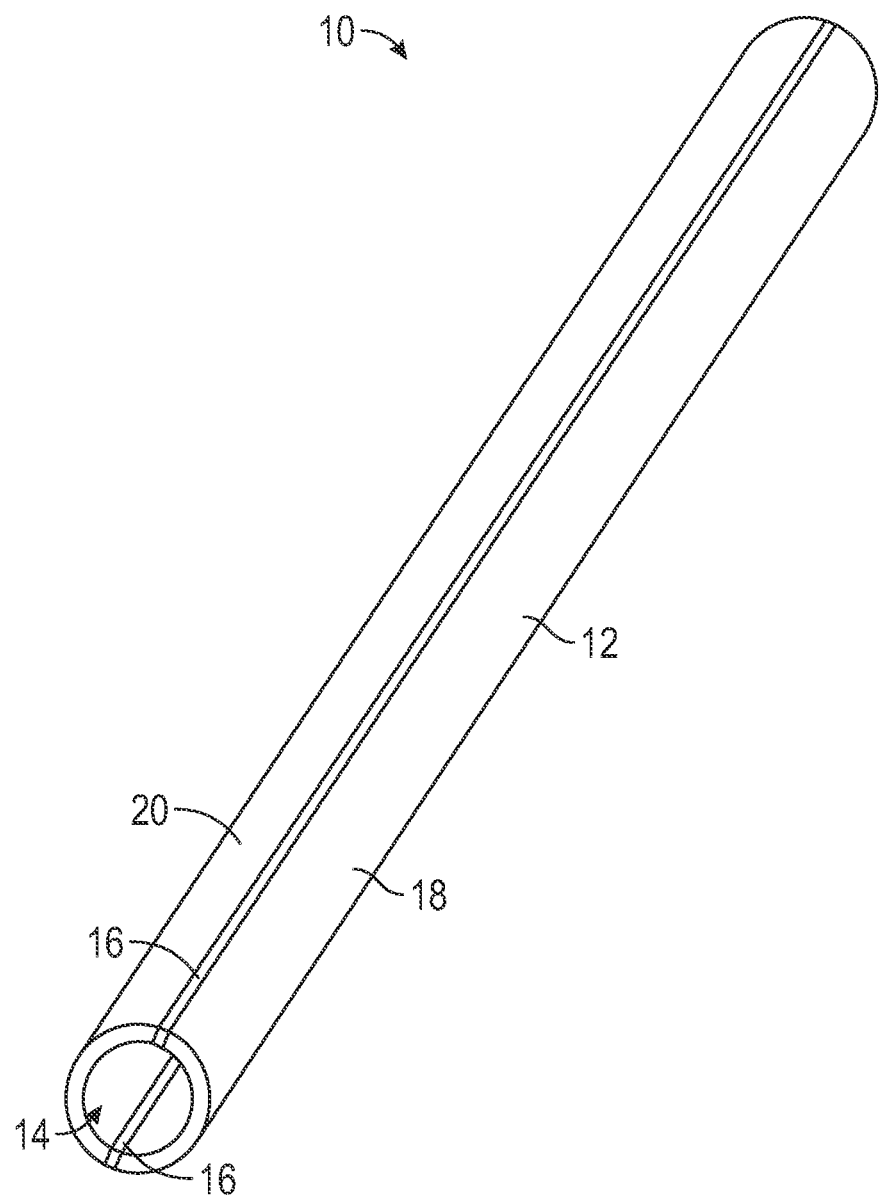
FIG. 1 is a perspective view of a peelable or splittable sheath according to an embodiment of the present invention, showing the sheath prior to peeling or splitting.

With reference to FIG. 1, a peelable or splittable sheath 10 of an introducer set or assembly is illustrated. The sheath 10 includes a substantially cylindrical or tubular main body portion 12 formed from two opposed, semi-circular walls 18, 20, and a pair of longitudinal stripes 16 or strips joined to the main body portion 12 and extending substantially the entire length of the sheath 10. The main body portion 12 and the stripes 16 define an interior passageway 14 of the sheath 10. The longitudinal stripes 16 have a wall thickness that is substantially equal to a wall thickness of the main body portion 12 and are formed on opposite sides of the sheath 10 (e.g., 180 degrees apart). While FIG. 1 illustrates two opposed stripes 16, it is contemplated that the sheath 10 may have a single stripe, or more than two stripes, without departing from the broader aspects of the invention. Where more than two stripes are utilized, they may be equally or unequally spaced along the circumference of the sheath 10.

In an embodiment, the main body portion 12 is formed from a first material, and the stripes 16 are formed from a second material that is different from the first material. The first material may be, for example, medium-density polyethylene (MDPE), high-density polyethylene (HDPE) or polypropylene (PP). More preferably, the first material is MDPE modified with a friction-reducing additive, or HDPE modified with a friction-reducing additive. In an embodiment, the friction-reducing additive may be a non-leaching siloxane additive, although other additives that impart lubricity and remove tackiness from the stripes, as discussed below, can be utilized.

The second material is preferably a thermoplastic elastomer (TPE) having a Shore A durometer of between about 37 and about 53, modified with a siloxane additive that functions to decrease the tackiness of the second material. The functionality of the stripes 16 and the peel strength required to split the sheath 10 lengthwise along the stripes 16 is dependent on the durometer of the stripes. Stripe materials with a lower durometer decreases the peel strength, while materials with a higher durometer increase the peel strength. It has been discovered that a TPE having a Shore A durometer in the range noted above, with a siloxane additive, provides for an optimal peel strength while minimizing tackiness of the material.

In the preferred embodiment, the stripes 16 are quite narrow in relation to the circumference of the sheath 10, and may be, for example, less than 1/16 inches in width. More preferably, the stripes 16 have a width in the circumferential direction about a few thousandths of an inch (e.g., 0.002-0.005 inches) to substantially hide them from view.

In one embodiment, a 5 French sheath has a main body portion 12 formed from A Dow MDPE modified with a siloxane additive to be approximately 5% active, and stripes 16 that are formed from Teknor Apex Medalists TPE likewise modified with a siloxane additive to be approximately 5% active.

Figure 2:
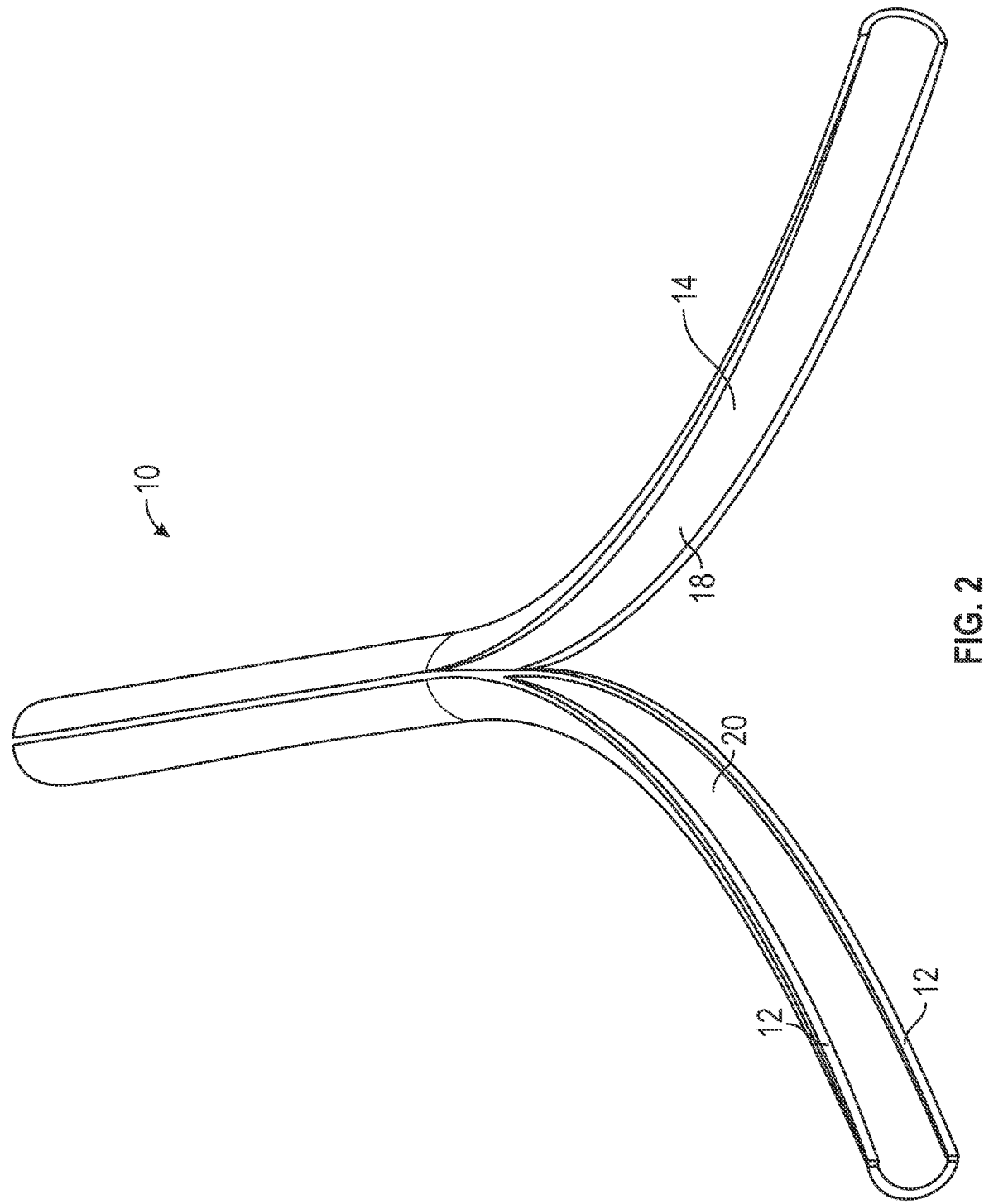
FIG. 2 is a perspective view of the peelable or splittable sheath of FIG. 1, illustrating peeling or splitting of the sheath along opposed peel stripes.

FIG. 2 illustrates the sheath 10 of the present invention in a partially peeled or split state. As shown therein, the sheath 10 is split in half at the stripe/main body portion interface. In an embodiment, handles (not shown) may be integrated with the sheath 10 to aid in splitting.

Figure 3:
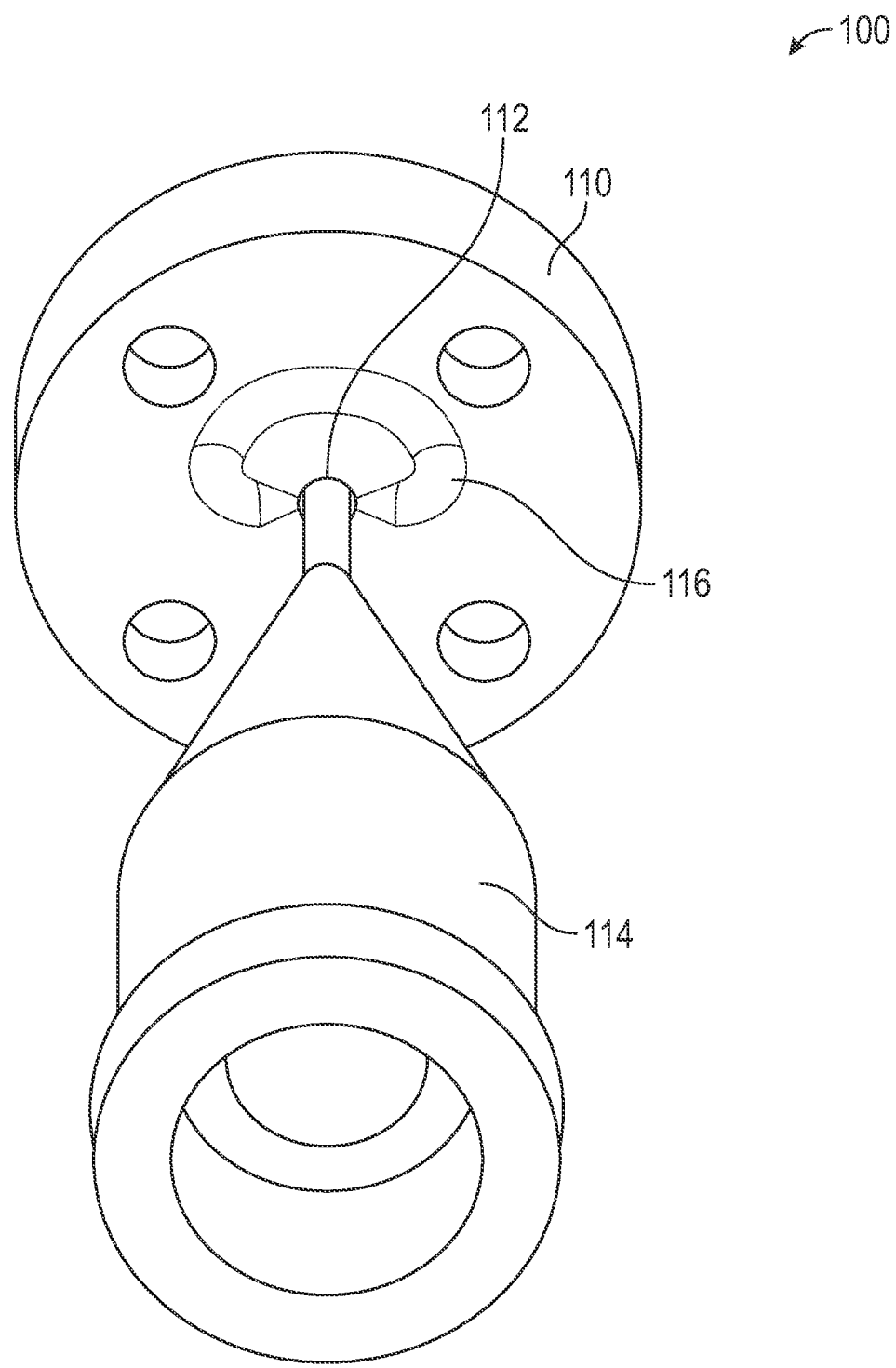
FIG. 3 is a perspective view illustrating an extrusion head of an extrusion assembly, utilized in the manufacture of the peelable or splittable sheath of FIG. 1, according to an embodiment of the invention.
Figure 4:
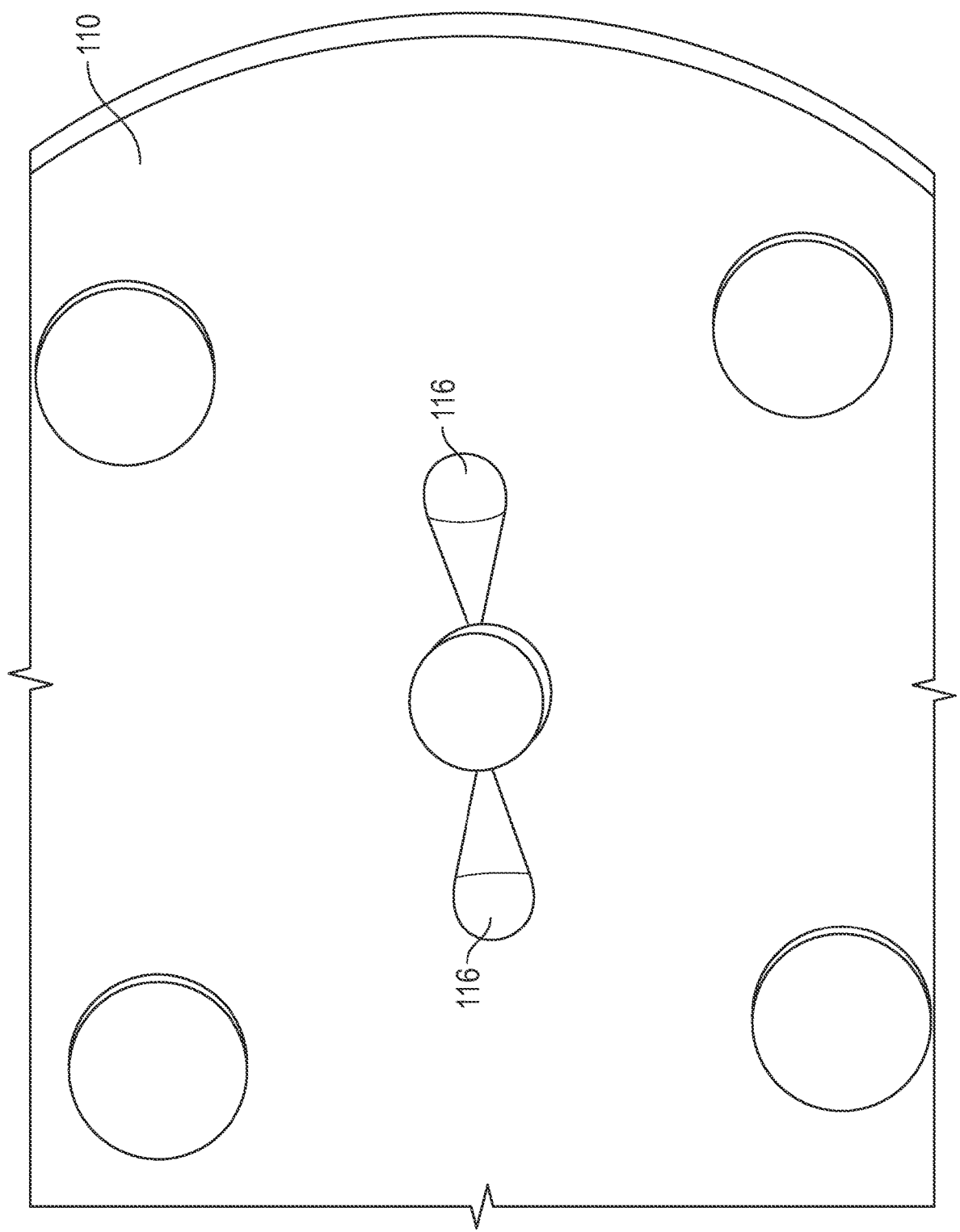
FIG. 4 is an enlarged, rear perspective view of a die of the extrusion head of FIG. 3.

The sheath 10 of the present invention is manufactured using a coextrusion process, where a primary melt stream that eventually forms the main body portion 12 and a secondary melt stream that eventually forms the stripes 16 are fed to a head comprising a die (which forms the outside diameter of the sheath 10) and a mandrel or tip (which forms the inside diameter of the sheath 10). FIG. 3 is a rear (upstream to downstream), perspective illustration of an extrusion head 100 that may be utilized to manufacture the sheath 10 of the present invention. As shown therein, the head 100 includes a die 110 having a central opening 112 within which is concentrically mounted a mandrel or tip 114. The back side of the die 110 is formed with feed channels 116 located 180 degrees apart that allow the secondary melt stream to run from a feed to the tip 114. FIG. 4 is an enlarged view of the die 110 showing the opposed channels 116 through which the secondary melt stream flows, according to one embodiment of the invention.

Figure 6:
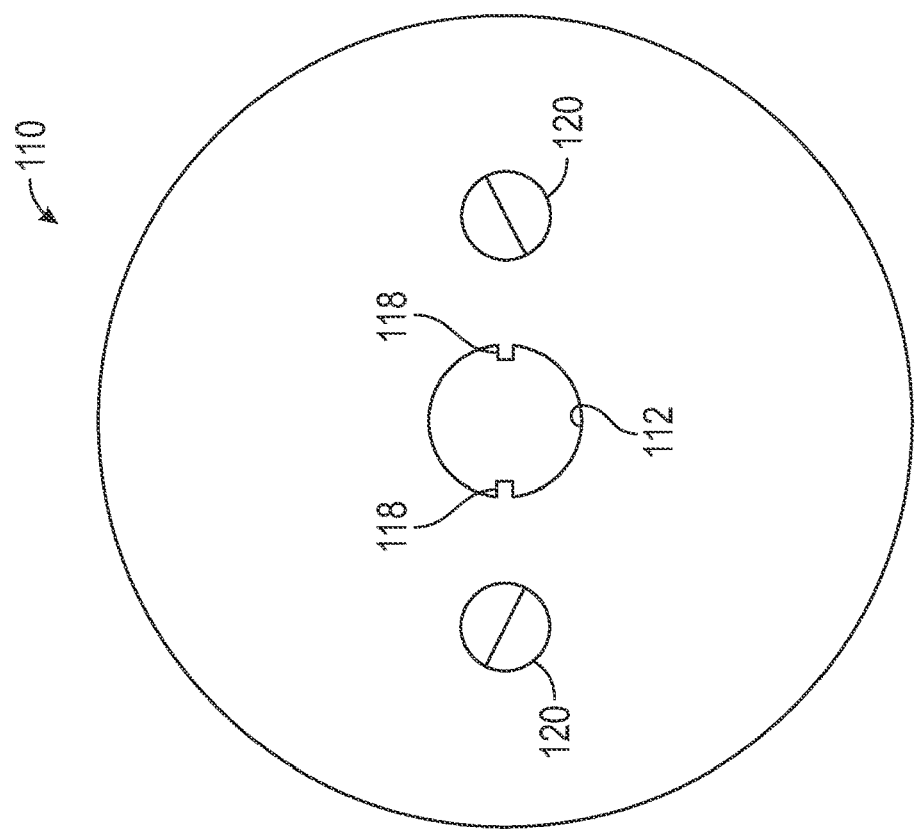
FIG. 6 is an end view of the die of FIG. 4.

Referring now to FIG. 5, a front view of the die 110 is shown. As shown therein, the central opening 112 includes a pair of opposed baffles 118 that project radially inward. Importantly, the outlets of the feed channels 116 are precisely aligned (angularly) with the baffles 118. FIG. 6 is an end view of the die 110 showing the location of the outlets 120 of the feed channels 116 in relation to the baffles 118 in the central opening 112. In an embodiment, the width of the baffles 118 are selected to generally correspond to the desired width of the peel stripes 16. In particular, in an embodiment, the baffles may be between about 0.003 inches and about 1/16 inches.

Figure 7:
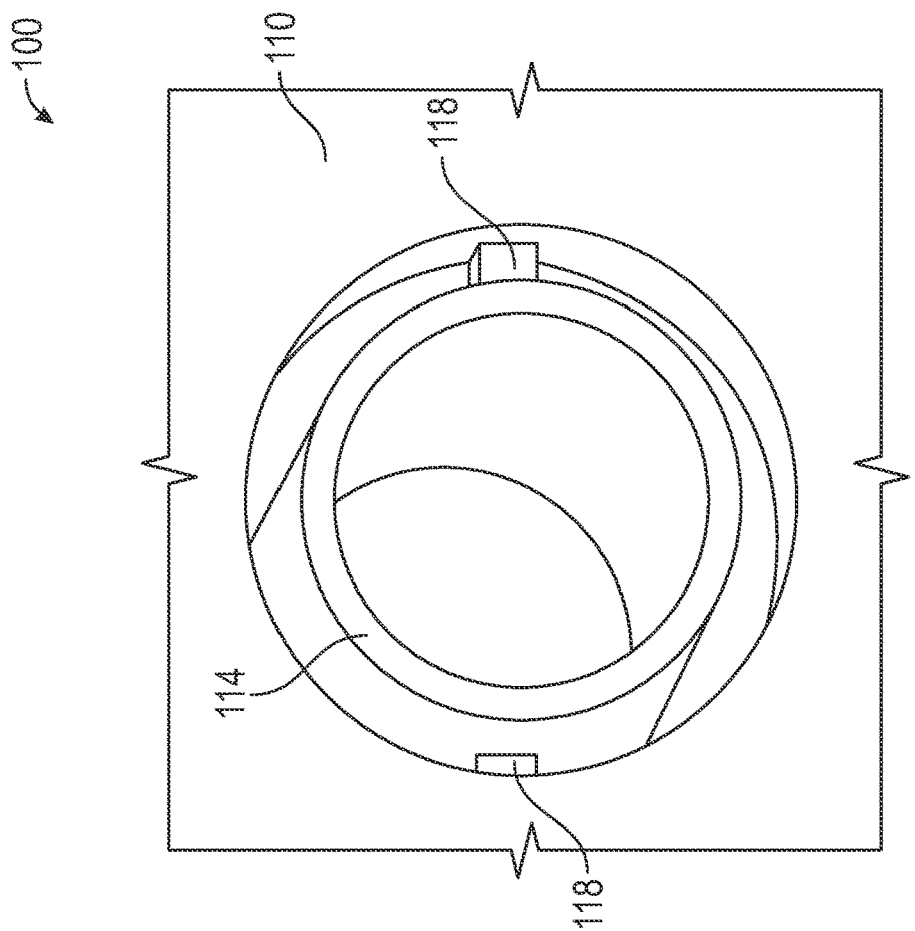
FIG. 7 is an enlarged, front perspective view of the extrusion head of FIG. 3, showing the die and mandrel.

With reference to FIG. 7, an enlarged, perspective view of a downstream end of the head 100 (including the die 110 and tip 114) is shown. Importantly, the baffles 118 block or inhibit the flow of the first material of the primary melt stream against the tip 114, creating a void where the second material from the secondary melt stream can enter the flow stream undisturbed to form the stripes 16. This tooling configuration, namely, the use of the baffles 118, ensures that the secondary melt stream is permitted to reach the tip 114. This, in turn, ensures that the stripes 16 extend all the way through the thickness of the sheath 10, which facilitates easy splitting of the sheath 10.

Figure 8:
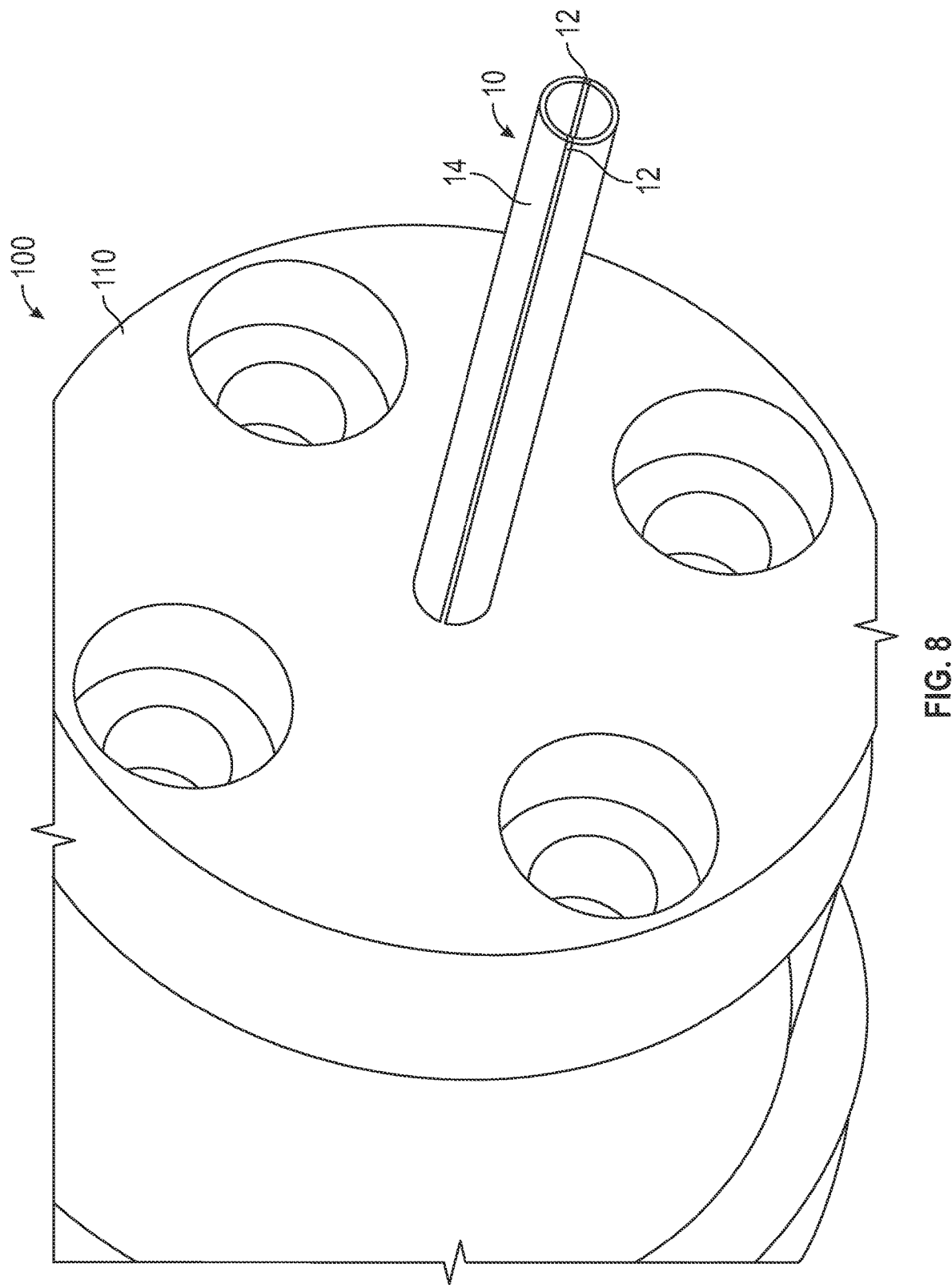
FIG. 8 is another perspective view illustrating the manufacture of the peelable or splittable sheath of FIG. 1, using the extrusion head of FIG. 3.

In operation, the first material that forms the main body portion 12 of the sheath 10 will flow into the head 100 from a primary extruder (not shown). A secondary extruder (not shown) will feed the second material that forms the stripes 16 through a port into the head 100. The second material that will form the stripes 16 will be diverted into two paths/channels 116 that are about 180 degrees apart and flow into the path of the primary melt stream. Importantly, in an embodiment, a cylindrical core is positioned downstream from the tip 114, so that coextrusion of the main body portion 12 and stripes 16 take place over the cylindrical core. This extrusion process is illustrated in FIG. 8. Once the material cures to form the cylindrical sheath 10, the core can be removed (or the sheath removed from the core).

Importantly, coextruding the sheath 10 over a cylindrical core ensures that the sheath 10 is formed in a cylindrical shape and that the cylindrical shape is maintained during the duration of cure. In particular, extruding over a cylindrical core prevents the sheath from deforming into an oval (i.e., ovality) during the coextrusion and curing process, which is typically due to the use of differing materials for the main body portion and stripe. As discussed above, this has long been a problem with sheaths having a main body portion and stripes formed from dissimilar materials.

Alternatively, or in addition to extruding the sheath 10 over a cylindrical core, vacuum sizing may be utilized to ensure that the sheath 10 is formed in with a substantially circular cross-section, with no or minimal ovality. In particular, vacuum sizing may be used downstream from the extruder assembly to assist in forming the circular cross-section. In an embodiment, after exiting the extruder, the still molten extrudate is fed through a sealed chamber in which a vacuum is being drawn. The extrudate passes through a series of vacuum sizing bushes or plates and is formed into its final shape before cooling. Cooling in the vacuum bath may be using water or air.

In an embodiment, the materials chosen for the stripes and main body portion may varied to some degree depending on dimeter of the sheath and the wall thickness.

Although this invention has been shown and described with respect to the detailed embodiments thereof, it will be understood by those of skill in the art that various changes may be made and equivalents may be substituted for elements thereof without departing from the scope of the invention. In addition, modifications may be made to adapt a particular situation or material to the teachings of the invention without departing from the essential scope thereof. Therefore, it is intended that the invention not be limited to the particular embodiments disclosed in the above detailed description, but that the invention will include all embodiments falling within the scope of this disclosure.

What is claimed is:

1. A splittable introducer sheath, comprising:
a tubular main body portion formed from a first material; and
at least one stripe joined to the tubular main body portion along an entire length of the tubular main body portion, the at least one stripe formed from a second material different from the first material, the second material including a thermoplastic elastomer modified with a siloxane additive,
wherein the tubular main body portion is dividable longitudinally along the at least one stripe; and
wherein no siloxane additive is present in the tubular main body portion.

2. The splittable introducer sheath of claim 1, wherein:
the first material is one of a medium-density polyethylene modified with a friction-reducing additive or a high-density polyethylene (HDPE) modified with a friction-reducing additive.

3. The splittable introducer sheath of claim 2, wherein:
the at least one stripe comprises two stripes located approximately 180 degrees apart.

4. The splittable introducer sheath of claim 2, wherein:
the second material has a Shore A durometer between about 37 and about 53.

5. The splittable introducer sheath of claim 4, wherein:
the siloxane additive is a non-leaching siloxane additive.

6. The splittable introducer sheath of claim 5, wherein:
the first material is a medium-density polyethylene.

7. The splittable introducer sheath of claim 6, wherein:
the sheath is a 5 French sheath.

8. The splittable introducer sheath of claim 1, wherein:
the at least one stripe has a wall thickness that is substantially equal to a wall thickness of the tubular main body portion.

9. The splittable introducer sheath of claim 1, wherein:
the at least one stripe has a width in the circumferential direction that ranges between about 0.002 inches and about 0.005 inches.

10. The splittable introducer sheath of claim 1, wherein:
the at least one stripe has a width in the circumferential direction that is less than 1/16 inch.

11. A splittable introducer sheath, comprising:
a tubular main body portion formed from one of a medium-density polyethylene modified with a siloxane additive or a high-density polyethylene (HDPE) modified with a siloxane additive; and
at least one stripe joined to the tubular main body portion along an entire length of the tubular main body portion, the at least one stripe formed from a thermoplastic elastomer modified with a siloxane additive;
wherein the tubular main body portion is dividable longitudinally along the at least one stripe;
wherein the second material has a Shore A durometer between about 37 and about 53; and
wherein the at least one stripe has a width in the circumferential direction that ranges between about 0.002 inches and about 0.005 inches.

* * * * *